US009848958B2

(12) United States Patent
Matov et al.

(10) Patent No.: US 9,848,958 B2
(45) Date of Patent: Dec. 26, 2017

(54) GENERATING A DYNAMIC THREE-DIMENSIONAL OCCLUSOGRAM

(71) Applicant: Align Technology, Inc., San Jose, CA (US)

(72) Inventors: Vadim Matov, San Jose, CA (US); Jihua (Michael) Cheng, Cupertino, CA (US); Fuming Wu, Pleasanton, CA (US); Kenji Tan, Mountain House, CA (US)

(73) Assignee: Align Technology, Inc., San Jose, CA (US)

( * ) Notice: Subject to any disclaimer, the term of this patent is extended or adjusted under 35 U.S.C. 154(b) by 548 days.

(21) Appl. No.: 14/084,407

(22) Filed: Nov. 19, 2013

(65) Prior Publication Data

US 2015/0142400 A1 May 21, 2015

Related U.S. Application Data

(63) Continuation of application No. 12/610,663, filed on Nov. 2, 2009, now Pat. No. 8,587,582.

(51) Int. Cl.

*G06F 17/50* (2006.01)
*A61C 7/00* (2006.01)
*G06T 17/20* (2006.01)

(52) U.S. Cl.

CPC .............. *A61C 7/002* (2013.01); *G06T 17/20* (2013.01); *G06T 2210/12* (2013.01); *G06T 2210/41* (2013.01)

(58) Field of Classification Search

CPC ........... A61C 7/002; A61C 7/08; A61C 9/004; G06T 7/004; G06T 19/20; G06T 2219/2004; G06T 17/00; G06T 17/20; G06T 2210/12; G06T 2210/41; G06F 19/12

USPC ............................ 703/1, 6; 345/420; 433/24

See application file for complete search history.

(56) References Cited

U.S. PATENT DOCUMENTS 5,905,658 A 5/1999 Baba
6,334,853 B1 1/2002 Kopelman et al.
7,023,435 B1 4/2006 Litke et al.
7,027,642 B2 4/2006 Rubbert et al.
7,156,655 B2 1/2007 Sachdeva et al.
7,239,313 B2 7/2007 Liepa
7,428,481 B2 9/2008 Nikolskiy et al.
8,013,853 B1 9/2011 Douglas et al.
2002/0025503 A1 2/2002 Chapoulaud et al.
2003/0214501 A1 11/2003 Hultgren et al.
2005/0018901 A1* 1/2005 Kaufmann .............. G06T 17/20 382/154
2005/0095562 A1 5/2005 Sporbert et al.
2008/0182220 A1* 7/2008 Chishti .................... A61C 7/00 433/24

(Continued)

*Primary Examiner* — Eunhee Kim

(74) *Attorney, Agent, or Firm* — Brooks, Cameron & Huebsch, PLLC

(57) ABSTRACT

Methods and systems for generating a three-dimensional occlusogram are disclosed. One method includes determining a virtual three dimensional (3D) mesh model object of at least one tooth of a patient and displaying the determined virtual 3D mesh model object of at least one tooth of a patient wherein the 3D mesh model object includes a plurality of data sets associated with a set of occlusal information for the at least one tooth of the patient.

20 Claims, 19 Drawing Sheets

410

400

(56) References Cited

U.S. PATENT DOCUMENTS

| | | | | |
|---|---|---|---|---|
| 2011/0045428 | A1 * | 2/2011 | Boltunov | A61C 7/002<br>433/24 |
| 2011/0104630 | A1 * | 5/2011 | Matov | A61C 7/00<br>433/24 |

* cited by examiner

GENERATING A DYNAMIC THREE-DIMENSIONAL OCCLUSOGRAM

PRIORITY INFORMATION

This application is a Continuation of U.S. application Ser. No. 12/610,663, filed Nov. 2, 2009, now U.S. Pat. No. 8,587,582, the entirety of which is incorporated herein by reference.

BACKGROUND

The present disclosure relates generally to the field of dental treatment. More specifically the present disclosure relates to calculating and displaying occlusion data for a patient.

One dental treatment objective of orthodontics is to move a patient's teeth into an optimal final occlusion, or a position in which the teeth function optimally and are aesthetically pleasing to the patient. Appliances such as braces, which are often a bracket and arch wire system, are applied to the teeth of the patient by a dental treatment professional.

The brackets in the braces system are mounted on the surface of the teeth of a patient and the arch wire couples all of the brackets on the same jaw to one another. The arch wire can be incrementally tightened over time during office visits to the treatment professional, exerting a continual force on the teeth, gradually moving them toward a desired final position.

Another system for treating dental malocclusions has become available under the trade name Invisalign® System. The Invisalign® System can have multiple components. For example, one component available in the Invisalign® System is called ClinCheck® and allows practitioners to simulate treatment of teeth by observing and modeling multiple stages of tooth movement.

Based on the results of the ClinCheck® component, another component (i.e., dental appliances called aligners) can be utilized. Such dental appliances can be thin, clear, and/or plastic removable devices that can be created, for example, to correspond to each treatment stage of the ClinCheck® simulation.

The aligners can be manufactured using advanced computing device-controlled fabrication systems. In such manufacturing processes, each aligner can be worn by the patient for a period of time before it is exchanged for a next stage aligner intended to further reposition the teeth.

The Invisalign® System addresses many of the limitations of conventional braces. For instance, if the Invisalign® System dental appliance is made from a clear material, it can be virtually invisible and, therefore, more aesthetically pleasing for the patient.

In some applications, the Invisalign® System dental appliances can be generally less painful and/or uncomfortable than braces. Additionally, the Invisalign® System dental appliances can be removed to permit better oral hygiene by allowing access to the tooth surfaces rather than having the braces attached thereto and the arch wires spanning of them, thus being more healthy for the patient's teeth.

DETAILED DESCRIPTION

Figure 1:
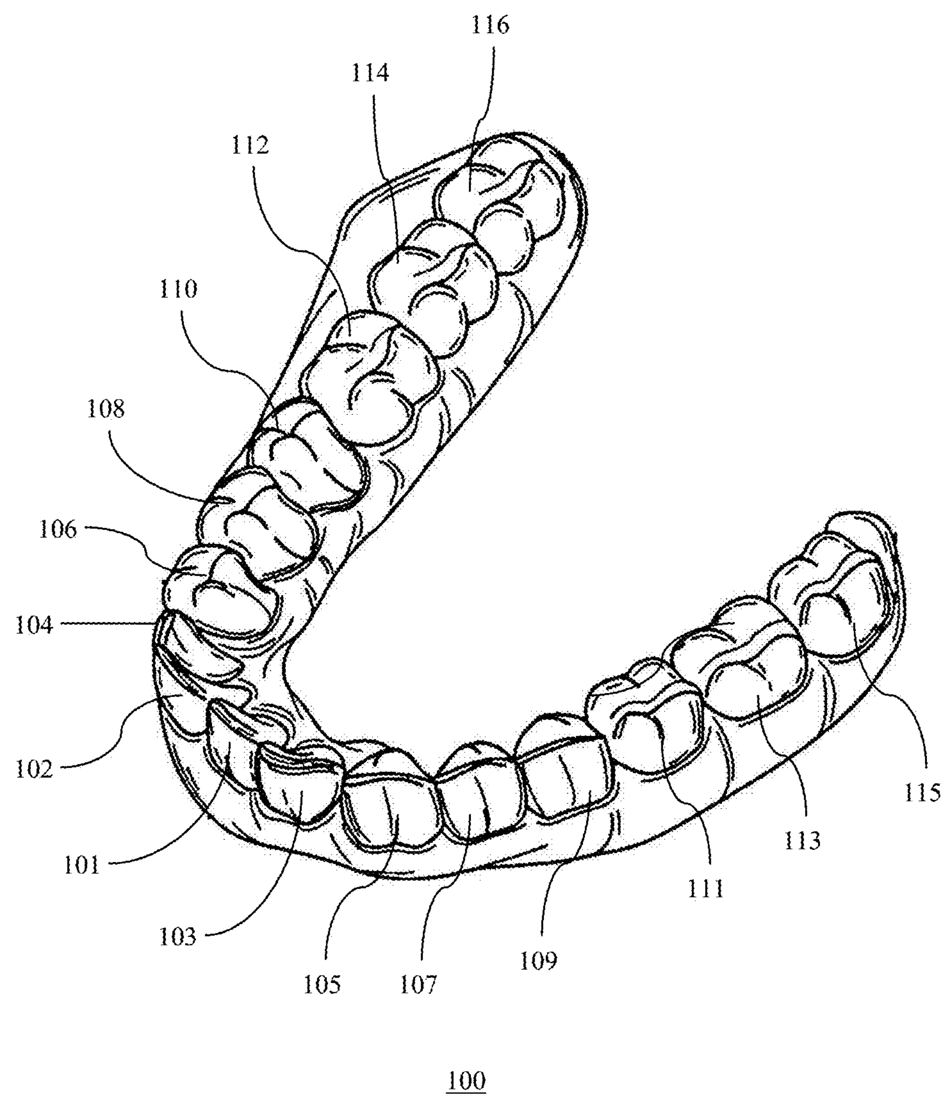
FIG. 1 is a diagram of the lower jaw and teeth of a patient's mouth.

FIG. 1 is a diagram of the lower jaw and teeth of a patient's mouth. Referring to FIG. 1, the lower jaw 100 of a patient may include teeth such as: the left central incisor 101, the right central incisor 102, the left lateral incisor 103, the right lateral incisor 104, the left cuspid or canine 105, the right cuspid 106, the left first bicuspid 107, the right first bicuspid 108, the left second bicuspid 109, the right second bicuspid 110, the left first molar 111, the right first molar 112, the left second molar 113, the right second molar 114, the left third molar or wisdom tooth 115, and the right third molar or wisdom tooth 116.

The upper jaw of a patient may have a similar set of incisors, cuspids, bicuspids, and molars. The relationship between the individual teeth of the jaw 100 and the relationship between the sets of teeth on the upper and lower jaws 100 are used to determine the corrective measures to be utilized in a chosen dental treatment procedure.

Different types of malocclusion (i.e., a non-optimal positioning of a patient's teeth) may include, among others, overbite (also known as class II malocclusion), underbite (also known as class III malocclusion), overjet, and diastema. One or more individual tooth orientations may also affect the type of chosen dental treatment procedure, such as crooked or rotated teeth.

Figure 2A:
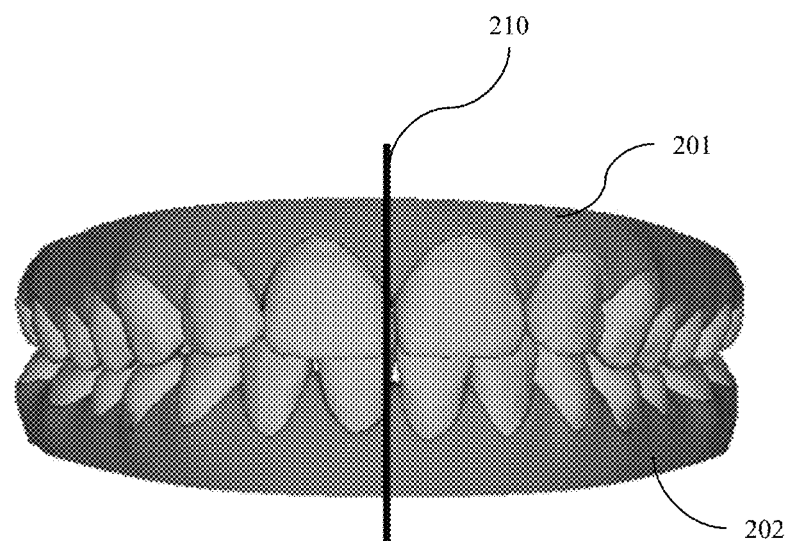
FIG. 2A-2B illustrate a virtual three-dimensional (3D) model of the segmented teeth of a patient.
Figure 2B:
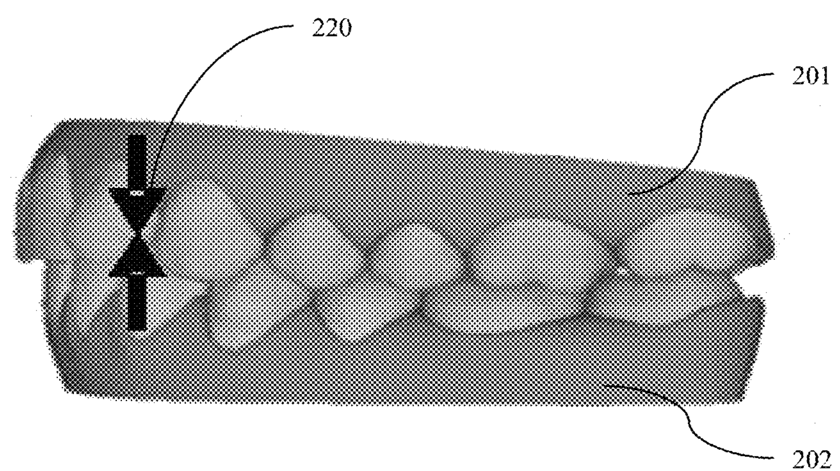

FIG. 2A-2B illustrate a virtual three-dimensional (3D) model of the segmented teeth of a patient. Referring to FIGS. 2A and 2B, the upper jaw 201 and the lower jaw 202 of a patient are shown in a generally optimal occlusion.

Referring to FIG. 2A, a frontal view of the patient's jaw in a closed bite position shows that the midline 210 between the upper central incisors is lined up with the midline between the lower central incisors, while a side view of the patient's jaw, FIG. 2B, shows a general lack of overlapping or space 220 between the upper and lower jaws of a patient. These, among others, can be treatment goals of dental treatment professionals when choosing a dental treatment for a patient.

Figure 3A:
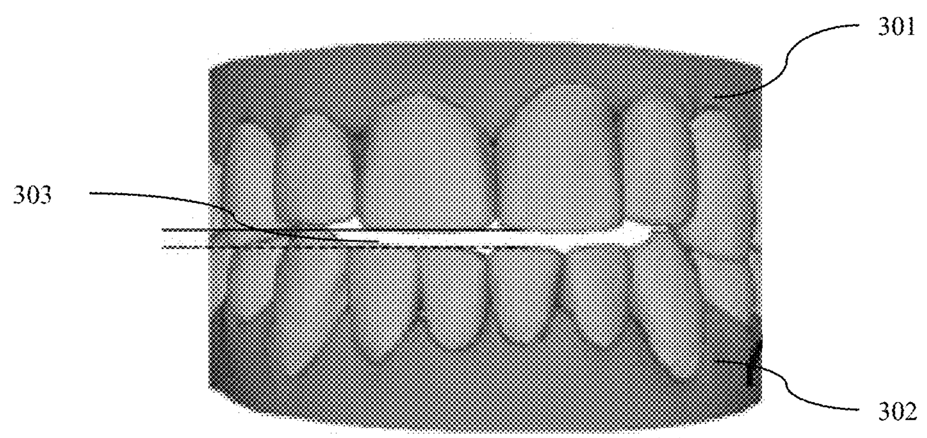
FIG. 3A-3B illustrate examples of a few possible types of malocclusion of a patient.
Figure 3B:
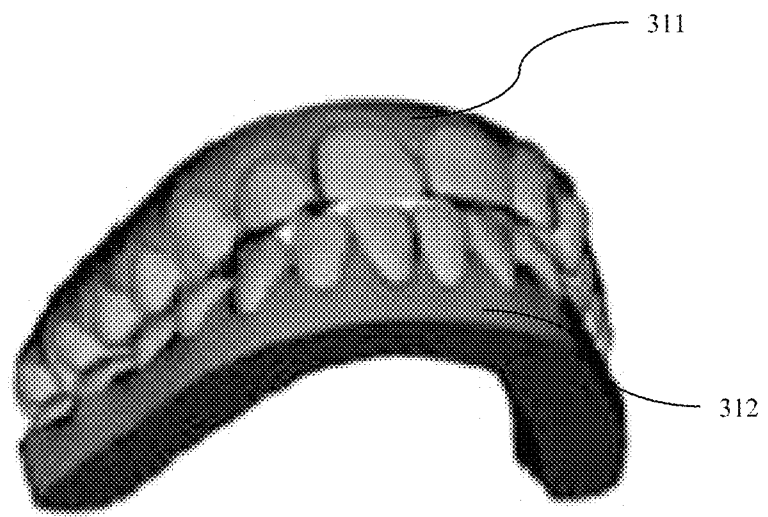

FIG. 3A-3B illustrate examples of a few possible types of malocclusion of a patient. FIG. 3A is a frontal view of the teeth of a patient, showing a gap 303 between the upper jaw 301 and the lower jaw 302 of a patient, when the patient's mouth is closed. This may be an indication of an open bite, or possibly an overbite malocclusion.

From a two-dimensional (2D) frontal perspective alone, it can, in some instances, be difficult to determine the extent and the exact type of malocclusion. FIG. 3B is a 3D model view of a patient's upper 311 and lower 312 jaws. FIG. 3B seems to indicate that the patient is suffering from an overjet malocclusion. As can be seen from FIG. 3A and FIG. 3B, in some instances, it may be more difficult, for treatment professional to determine the extent of the occlusal state of a patient's mouth from a 2D representation than from a 3D representation.

Figure 4:
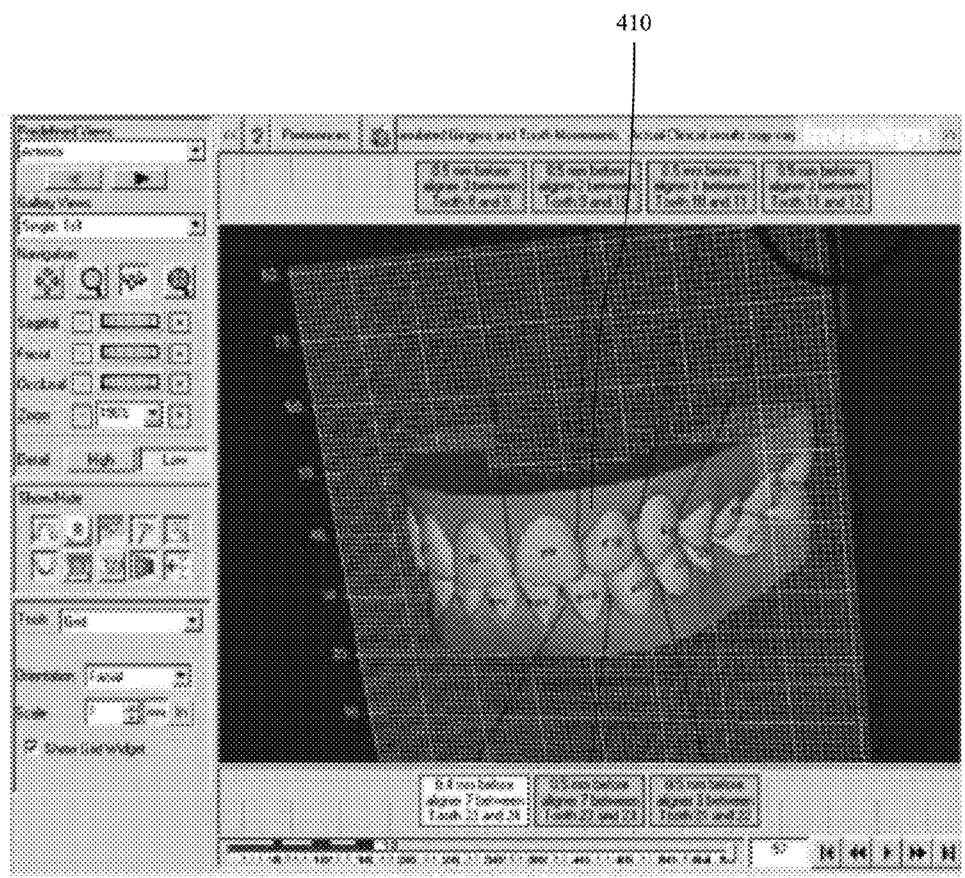
FIG. 4 illustrates a virtual 3D model of the teeth of a patient.

FIG. 4 illustrates a virtual 3D model of the teeth of a patient. Referring to FIG. 4, a 3D software environment 400 may be used to view a virtual 3D model of the teeth 410 of a patient where the software includes executable instructions executed by a processor to manipulate patient mouth data based on the actual features of the mouth of the patient stored in memory to create a virtual 3D model of the teeth 410 of the patient. For example, the data can include shape and/or positioning information about features of one or more teeth, gingival structures, bone structures, and/or other dental features.

The 3D software environment 400 may include any 3D software environment used to view and/or manipulate a virtual 3D model of a patient's teeth 410. In some embodiments of the present disclosure, the virtual 3D model of a patient's teeth 410 may be rotated about any of the X, Y, and/or Z axes of the 3D space to allow for viewing by the treatment professional of one or more angles of the jaw and teeth 410 of a patient.

Figure 5:
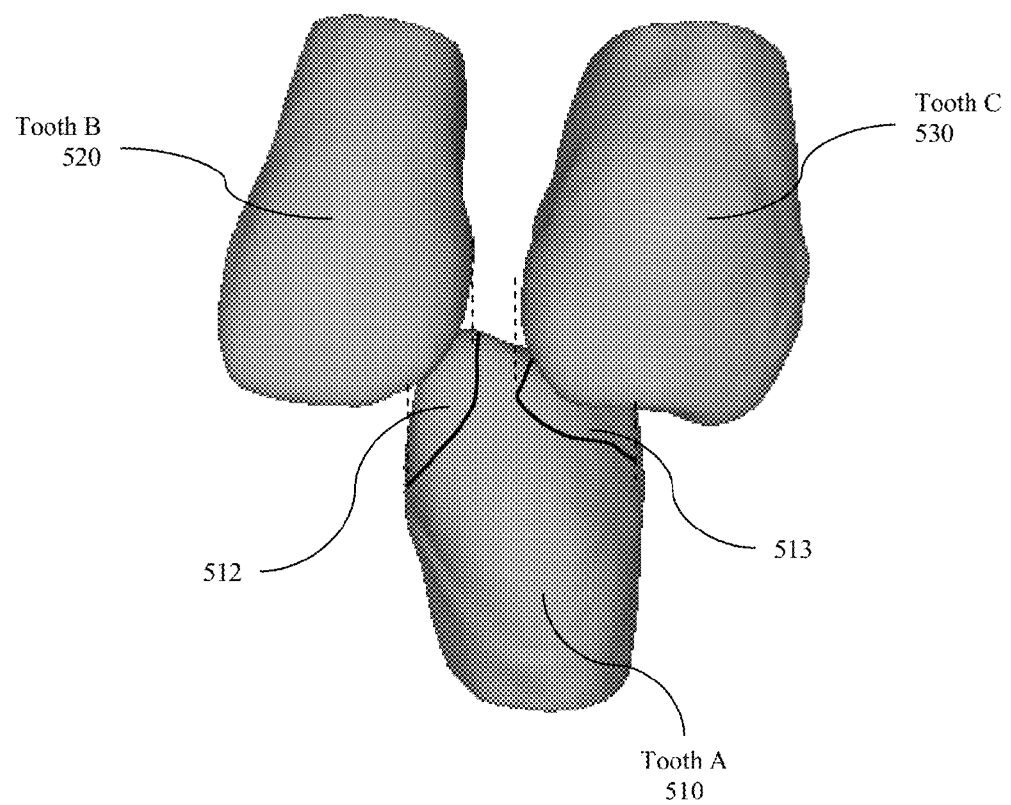
FIG. 5 illustrates the occlusal area of a tooth.

FIG. 5 illustrates the occlusal area of a tooth. Referring to FIG. 5, Tooth A 510, represents a tooth on the lower jaw of a patient. Tooth B 520 and Tooth C 530 represent teeth on the upper jaw of a patient. When a patient bites down the teeth on the upper jaw impact with the tooth on the lower jaw. The impact force, or lack thereof, on any tooth in the mouth is dependent upon the position of the teeth of the patient when the mouth is in the closed position, and this force may be calculated and quantified.

The position of the teeth of a patient may determine the area of contact and/or the contact distance between teeth on the upper jaw with teeth on the lower jaw. The area of contact between teeth may be different, for instance, due to such factors as the horizontal misalignment of teeth, while the collision depth between teeth may be due to factors such as, among others, the vertical misalignment of teeth. In the case of malocclusions such as diastema, or a gap between teeth, for example, it may be possible that a tooth, or a portion of a tooth, has no impact force acting upon it. The impact force on a tooth from other teeth in the mouth of a patient may be a contributing factor to the direction and/or extent of movement that a tooth may incur during a possible dental treatment process.

As used herein, the occlusal area of a tooth refers to the area in which an impact force may be involved. Referring to FIG. 5, for example, the occlusal area of Tooth A 510 due to Tooth B 520 is shown by the area 512, while the occlusal area of Tooth A 510 due to Tooth C 530 is shown by the area 513.

Figure 6:
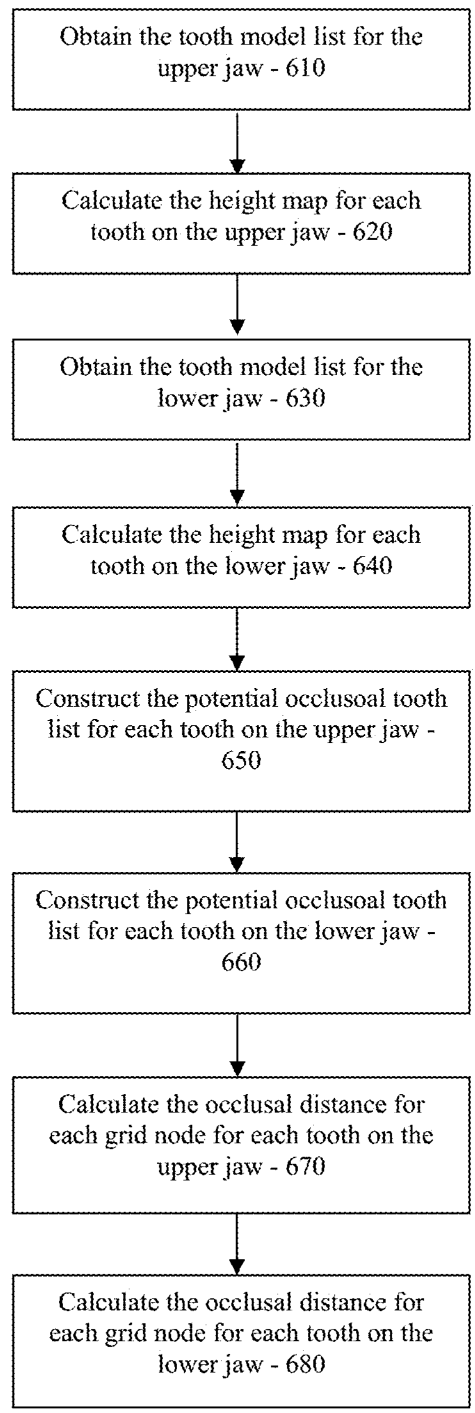
FIG. 6 is a flowchart illustrating a process for calculating occlusal information in an embodiment of the present disclosure.

FIG. 6 is a flowchart illustrating a process for calculating occlusal information in an embodiment of the present disclosure. In various embodiments of the present disclosure, occlusal information may be used to build, and/or model, an occlusogram and/or a virtual model of a patient's teeth displaying the occlusal information of the patient. In order to calculate the occlusal information for the teeth of a patient, the number, type, position, and/or location of one or more of the teeth of a patient may be determined. That is, for example, in one aspect, a list of teeth on the upper jaw of a patient can be obtained 610, for example from data stored in memory.

From the list of teeth on the upper jaw, a height map and/or distance field can be calculated or otherwise determined for each tooth on the upper jaw 620. In some embodiments, the height map and/or distance field include an array of numeric values relating to the crown of the tooth as described in further detail below. Since occlusal information relates to the relationships between the teeth on the upper and lower jaws, a tooth model list for the lower jaw can also be obtained 630 and/or the height map and/or distance field of each tooth on the lower jaw can be calculated or otherwise determined 640.

Still referring to the embodiment illustrated in FIG. 6, once the height map and/or distance field values for each tooth of the upper and lower jaws have been calculated, a potential occlusion tooth list for each tooth on the upper 650 and lower 660 jaws can be determined. In one aspect, the potential occlusion tooth list for a tooth can include a listing of teeth that may affect the occlusion data of that particular tooth, that is, which teeth in the mouth of the patient may contact each other and in doing so provide a force that may effect the movement of the particular tooth in the event a dental treatment process is undertaken. If a potential occlusion tooth list is constructed for each tooth, then the occlusal distance for each tooth on the upper 670 and lower 680 jaws can be calculated or otherwise determined based on, for example, the space and/or collision depth between upper teeth and lower teeth of a patient.

Figure 7:
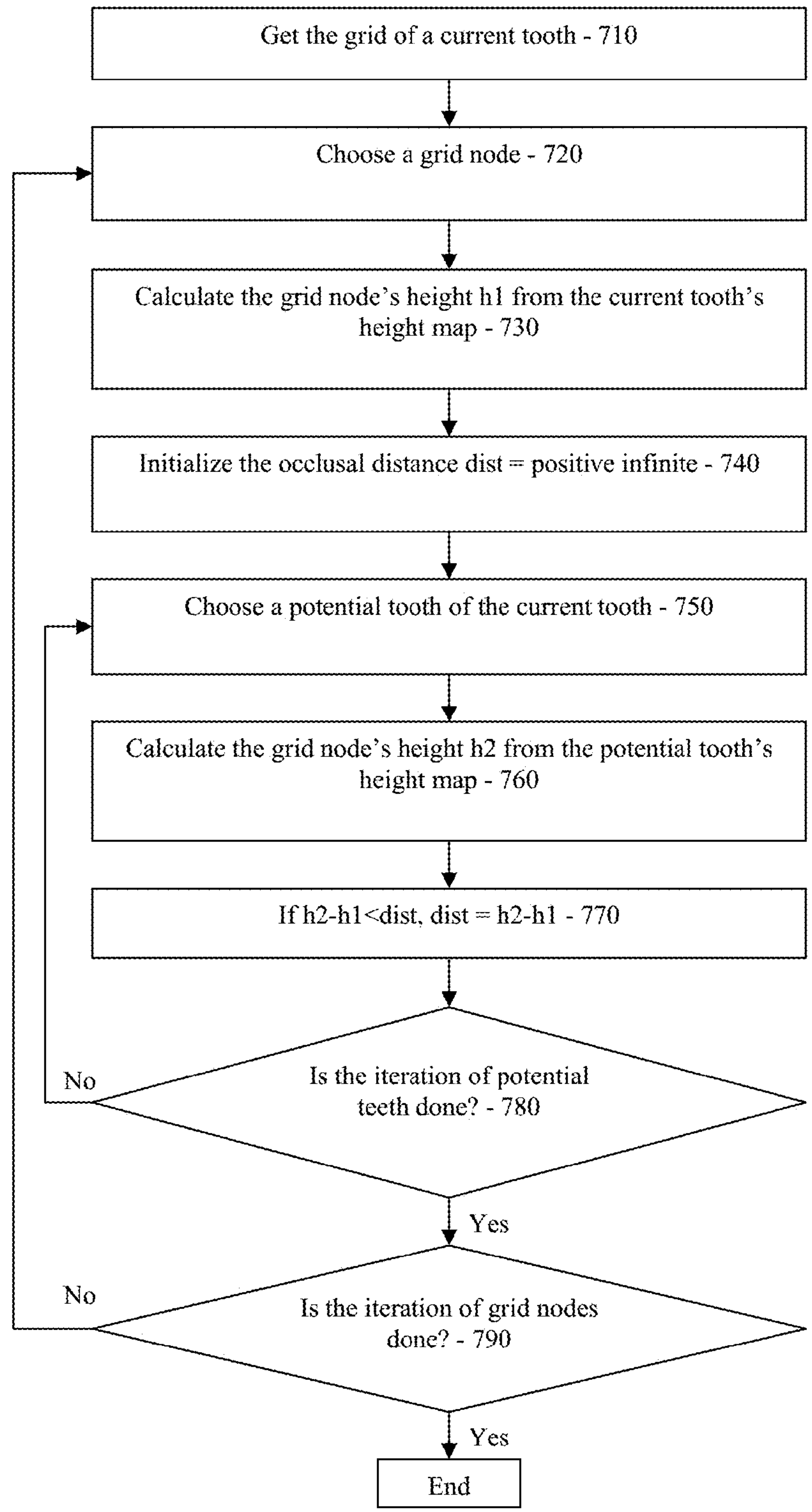
FIG. 7 is a flowchart illustrating a process for determining the occlusogram data of a tooth of a patient based on an embodiment of the present disclosure.

FIG. 7 is a flowchart illustrating a process for determining the occlusogram data of a tooth of a patient based on an embodiment of the present disclosure. As used herein, occlusogram data is the calculated data set that may be used for modeling a virtual 3D occlusogram model, or may be used by a treatment professional, with or without the aid of a computing device processor and algorithm stored in memory, to incorporate the information into a predictive model from a possible treatment process. As used herein, the term virtual refers to items or processes created, simulated, and/or carried on by means of a computing device and/or computing device network.

Referring to FIG. 7, in some embodiments of the present disclosure, the occlusogram data may be calculated by using a virtual grid of a 3D model of a tooth as the initial base 710 and constructed, for example, as discussed below. The grid of a 3D model of a tooth (or referred to as the surface grid of a tooth) may include a 3D mesh outlining the tooth. The surface grid may be constructed of a plurality of 2D polygons, for example, triangular in shape, situated in a 3D space, and coupled in such a manner as to create the surface of a 3D model.

The density of the surface grid may be variable or constant. For example, a variable density may have a higher density grid at the more curved geometrically complex areas of the tooth surface, and a lower density at the flatter, less geometrically complex area. In some instances, the denser the surface grid, the longer it takes to model the 3D object. However, in some instances, the less dense the surface grid, the lower the quality and resolution of the 3D model are. Thus, in such instances, it may be desirable to have a variable density surface grid to optimize the time it takes to generate the 3D model without sacrificing quality and/or resolution.

Referring still to FIG. 7, once a surface grid of a tooth has been obtained, a first surface grid node can be chosen 720. As used herein, a surface grid node is a point at which the lines used to form the polygons of the surface grid intersect. A denser area of a surface grid will have more surface grid nodes than an area that is less dense.

For example, in the embodiment of FIG. 7, for the first surface grid node, the surface grid node's height, h1, can be calculated from the height map of the current tooth 730. The height of the surface grid node may be taken as a signed distance from a plane generally parallel to the occlusal surface, or the biting surface, of a tooth, as described in further detail below. Another data value that can be utilized is the occlusal distance. As used herein, the occlusal distance is a value based on the space or contact depth between the current tooth and other teeth.

For example, to calculate the occlusal distance, the occlusal distance value can be first initialized. As shown in FIG. 7, in one aspect, the occlusal distance can be initialized as a positive infinite quantity 740. Once the occlusal distance value is initialized, a first potential occlusion tooth can be chosen 750 and the height of the surface grid node, h2, can be calculated from the potential tooth height map 760 which is a map of the teeth that can potentially interact with the first potential occlusion tooth. If a distance field is used in calculating the occlusal distance, (see the details below), the closest distance, d2 (i.e., the location of the corresponding closest point on the first potential occlusion tooth) can be calculated from the distance field of the occlusion tooth.

For example, in the case of the height map, if $h2-h1<dist$, then $dist:=h2-h1$, where dist is the occlusal distance between the current tooth and the potential tooth 770.

In the case of usage of the distance field, if $d2<dist$, then $dist:=d2$.

In the case that the current tooth has more than one potential occlusion tooth, a next occlusion tooth can be chosen 750, and the height 760 (and/or closest distance to the next tooth) and occlusal distance 770 can be calculated. This can be repeated for all occlusion teeth associated on the occlusion teeth list for the current tooth 780.

Once all the heights and occlusal distances for the first node are determined, a check can be performed to see if the values for all of the nodes of the current tooth surface grid have been calculated 790. If not, a next tooth surface node can be chosen 720 and the heights (and/or closest distances) and occlusal distances for the next tooth surface node can be calculated 730-780, and the routine described above is repeated for each grid node of the tooth. In various embodiments, once the heights, and/or closest distances and occlusal distances for each grid node of the tooth are calculated, the data may be used for constructing a virtual 3D occlusogram.

In some embodiments it can be beneficial to use the height maps to compute occlusal distances for posterior teeth and to use the distance fields to compute the occlusal distances for anterior teeth.

Figure 8:
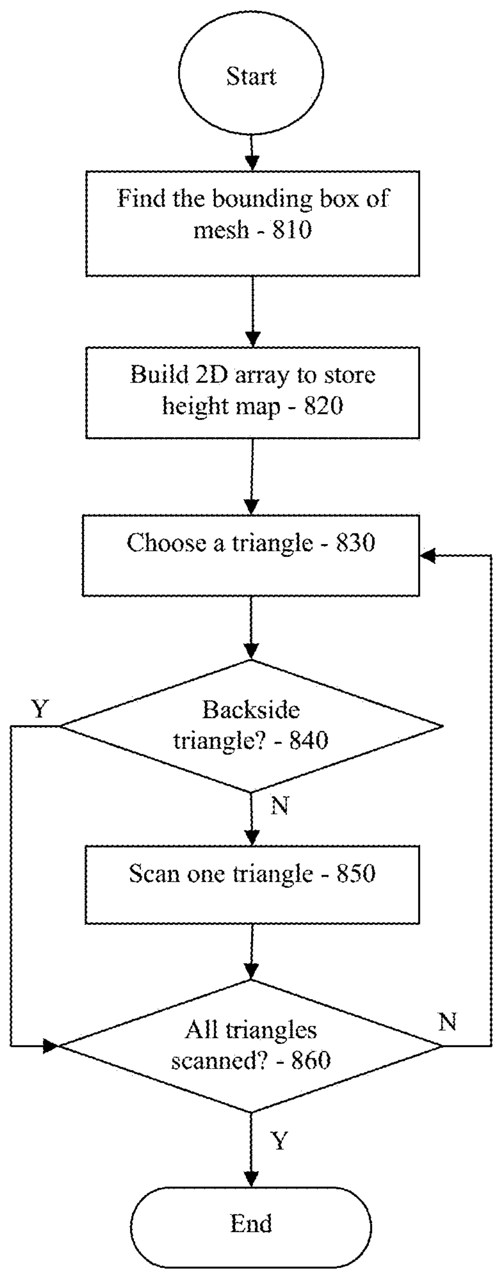
FIG. 8 is a flowchart illustrating the process of building a height map in one aspect based on an embodiment of the present disclosure.

FIG. 8 is a flowchart illustrating the process of building a height map in one aspect based on an embodiment of the present disclosure. Referring to FIG. 8, to build a height map from the mesh of a tooth, the height map can, for example, be built by determining a bounding box of the mesh of the tooth 810 (see FIG. 11B). As used herein, a bounding box may be used as the basis for the definition for the 2D planar grid (see FIG. 11C) for use in one or more steps of the procedure of building a height map from the mesh of a tooth.

In various embodiments, the array for storing the height map values must be built 820 with initial values of the array set to a maximum negative value. As used herein, the height map is a 2D array data structure that stores the vertical height of a tooth's crown surface. Also, as used herein, the crown surface of a tooth is the area of a tooth that is located above the gum-line, or in other words, the visible portion of a tooth and the vertical height can be defined by designer of the software or, in some instances, chosen by the user of the software.

In the height map array, the indices of the array represent a point in x and y coordinates, where the x-y plane is the occlusal plane of the lower jaw of a patient, which is generally parallel to the biting surface of the tooth, in many instances. The value of the array element at each index of the array is the z value at the point in the x-y plane. This z value is the height of the tooth's crown surface at the chosen point.

In some embodiments, the distance field of a tooth is a 3D array data structure corresponding to a 3D grid with generators defined by a bounding box of the tooth. The granularity of step detail of 3D grid can be chosen to be comeasurable with the level of relevant details of the tooth's occlusal surface. Each element of the 3D array data structure can have, stored therein, the coordinates of the closest point on the tooth's surface to the corresponding node of the 3D grid. Besides the coordinates, in some embodiments, the distance to the closest point, can be stored for efficiency purposes.

Referring still to FIG. 8, construction of the height map can be accomplished, for example, as follows: from the mesh of the chosen tooth, in one aspect, a first triangle is chosen 830 from the list of polygon surfaces comprising the mesh of the tooth. In various embodiments, any polygon on the surface of the tooth may be divided into one or more triangles for the purposes of scanning triangles to calculate height values.

If the chosen triangle is a backside triangle, that is, a triangle with a normal at more than a 90 degree angle with respect to the z direction, it can be ignored 840, in some embodiments. If the chosen triangle is not a backside triangle, the triangle can be scanned 850 as discussed with respect to FIGS. 9A and 9B. Once the triangle is scanned, it can be determined whether more triangles remain as a part of the mesh that have not yet been analyzed 860. Once all the triangles of the mesh of the tooth are scanned, and the height values are input into the height map array, the height map data set for the tooth is complete. A similar iteration routine over the set of the tooth surface mesh can be used for computing of the distance field of a tooth.

Figure 9A:
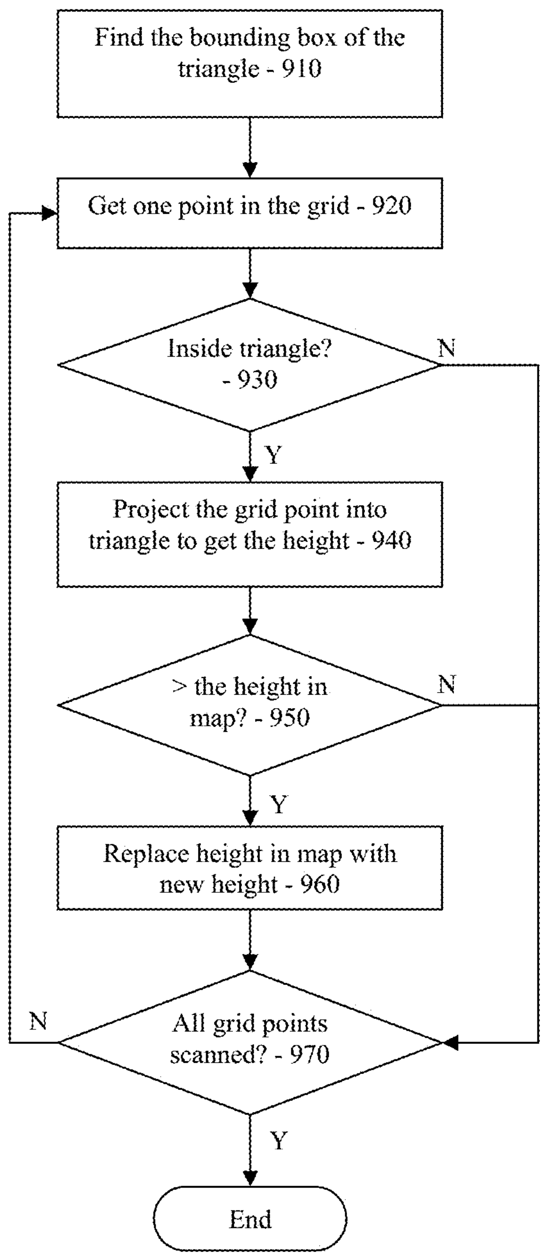
FIG. 9A is a flowchart describing a process for scanning a triangle for building a height map in one aspect based on an embodiment of the present disclosure.
Figure 9B:
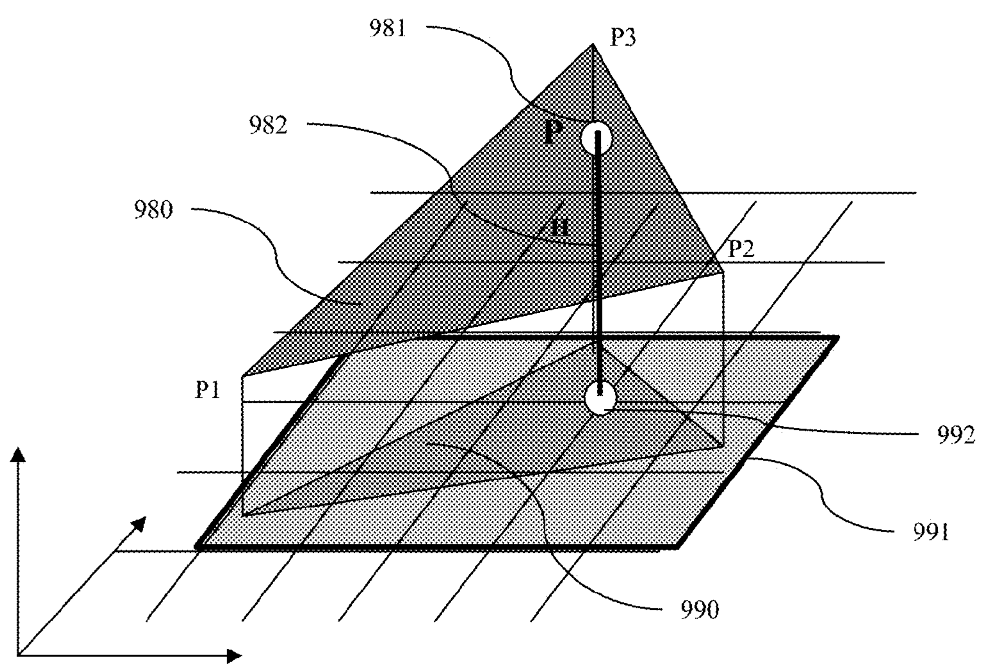
FIG. 9B is a diagram of a triangle for use in the process of scanning a triangle depicted in FIG. 9A based on an embodiment of the present disclosure.

FIG. 9A is a flowchart describing a process for scanning a triangle for building a height map in one aspect based on an embodiment of the present disclosure. FIG. 9B is a diagram of a triangle for use in the process of scanning a triangle depicted in FIG. 9A based on an embodiment of the present disclosure.

Referring to FIGS. 9A and 9B, in some embodiments of the present disclosure, scanning triangles on the surface of the tooth may be used in the process of building a height map for the tooth. In some embodiments, a bounding box 991 of the triangle is determined (FIG. 9A, 910). As used herein, a bounding box 991 is the smallest box created on a 2D planar grid that fully surrounds a projection 990 of the triangle 980 onto the grid. In the embodiment of FIG. 9A, the triangle is formed by vertices P1(x1,y1,z1), P2=(x2,y2,z2), and P3=(x3, y3, z3).

Referring to FIGS. 9A-9B, from within the bounding box 991, a first grid node 992 can be chosen (FIG. 9A, 920). The grid node 992 can be projected as point P 981, where P=(x,y,z), where, for example, x and y are known, and z is unknown.

Point P 981 may be decomposed as $P=\alpha\cdot P2+\beta\cdot P3+(1-\alpha-\beta)\cdot P1$, with three variables ($\alpha$, $\beta$, z). It can be checked to see if the grid node 992 is located within the projection 990 of the triangle 980 (FIG. 9A, 930). If $\alpha$, $\beta$ and $(1-\alpha-\beta)$ are all inside [0,1], then this grid point is inside the triangle.

The height of the node 992, H 982, can be calculated as: $H=\alpha\cdot(P2,Z)+\beta\cdot(P3,Z)+(1-\alpha-\beta)\cdot(P1,Z)$, where Z is the unit vector in the Z direction, which is the distance between the grid point 992 and the projected point P 981 (FIG. 9A, 940). In some embodiments, the height, H 982, can be compared to the height currently assigned to the height map for the grid node 992 (FIG. 9A, 950).

If this height 982 is greater than the height currently assigned in the height value of node 992 in the height map, then the height 982 of the current grid node projection point 992 can be used to replace the height value in the height map (FIG. 9A, 960). These steps can be repeated for each grid node located within the bounding box 990 (FIG. 9A, 970).

Figure 10A:
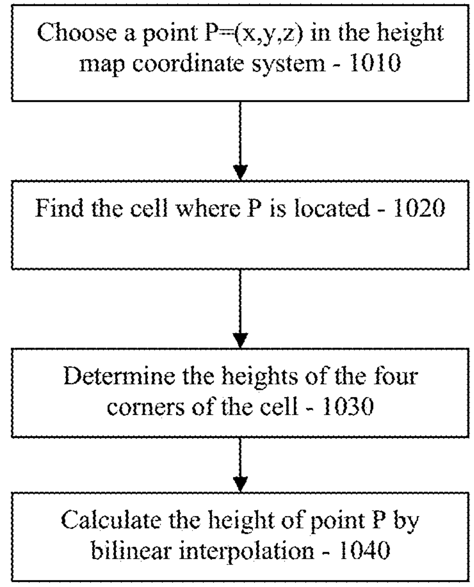
FIG. 10A is a flowchart illustrating a process of calculating occlusal distance in an embodiment of the present disclosure.

FIG. 10A is a flowchart illustrating a process of calculating occlusal distance in an embodiment of the present disclosure. FIG. 10A is a flowchart illustrating a process of calculating occlusal distance in an embodiment of the present disclosure.

Figure 10B:
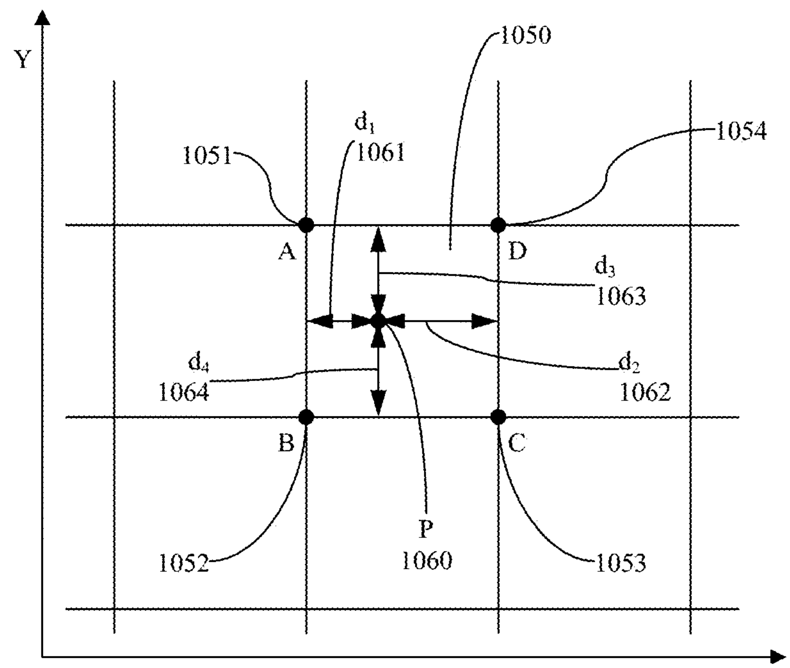
FIG. 10B illustrates determination of the height of a point by bilinear interpolation in an embodiment of the present disclosure.

Occlusal distance, which is a value based on the space and collision depth between upper teeth and lower teeth, can be an integral part of an occlusogram. Referring to FIGS. 10A and 10B, in various embodiments of the present disclosure, the occlusal distance may be calculated by making use of a tooth's height map. Occlusal distance may be calculated for any point P 1060 in the height map coordinate system (FIG. 10A, 1010), where point P 1060 is defined as P=(x,y,z).

For the point P 1060, the cell 1050 in the x-y plane, bounded by points A 1051, B 1052, C 1053, and D 1054, in which point P 1060 is located (FIG. 10A, 1020) is determined. Using the height map, heights for the cell 1050 corner points, A 1051, B 1052, C 1053, and D 1054 (FIG. 10A, 1030) is determined.

The height of the point P 1060 may then be calculated by the use of bilinear interpolation (FIG. 10A, 1040). The following equations may be used for the calculation of the height $H_P$ of the point P 1060:

$$H_{AB}=\left(\frac{d_4}{d_3+d_4}\right)\cdot H_A+\left(\frac{d_3}{d_3+d_4}\right)\cdot H_B$$

$$H_{DC}=\left(\frac{d_4}{d_3+d_4}\right)\cdot H_D+\left(\frac{d_3}{d_3+d_4}\right)\cdot H_C$$

$$H_P=\left(\frac{d_2}{d_1+d_2}\right)\cdot H_{AB}+\left(\frac{d_1}{d_1+d_2}\right)\cdot H_{DC}$$

where $H_A$ is the height of node A 1051 on the height map;
$H_B$ is the height of node B 1052 on the height map;
$H_C$ is the height of node C 1053 on the height map;
$H_D$ is the height of node D 1054 on the height map;
$d_1$ 1061 is the distance in the positive distance in the x direction on the x-y plane between point P 1060 and line AB;
$d_2$ 1062 is the distance in the positive distance in the x direction on the x-y plane between point P 1060 and line CD;
$d_3$ 1063 is the distance in the positive distance in the y direction on the x-y plane between point P 1060 and line AD;
$d_4$ 1064 is the distance in the positive distance in the y direction on the x-y plane between point P 1060 and line BC;

and $H_P$ is the calculated height of point P 1060.

In various embodiments, the construction of the distance field from a tooth under consideration can proceed through the following sequence of steps:

1. For all elements of the 3D array initialize the "closest distance" component to the value of the height of the corresponding node of the 3D grid.
2. Scan each of the triangles from the tooth's surface triangular mesh according to the following algorithm:
   a. If the chosen triangle is a backside triangle, that is a triangle with normal at more than 90 degrees angle with respect to the z direction, it is ignored.
   b. Compute the circumscribed sphere S of the triangle.
   c. Form the list of indices in 3D array such that for every index the distance form the corresponding 3D grid node to the center of the sphere S is not greater than sum of the radius of the sphere S and the current value of the "closest distance" component of the element of 3D array.
   d. For each index in the list formed on the previous step compute the distance from the corresponding node of the 3D grid to the triangle under consideration as well as the closest point on this triangle.
   e. If the distance computed on the previous step is smaller than the values of the current "closest distance", set the "closest distance" to the computed distance and the coordinates of the closest point to the coordinates of the closes point computed on the previous step.
3. For the points between the nodes of the 3D grid the value of the "closest distance" can be computed by multi-linear interpolation of the corresponding values of the nodes of the grid.

In one aspect, this process described above may be used to determine the occlusal distance of any point on a tooth mesh.

Figure 11A:
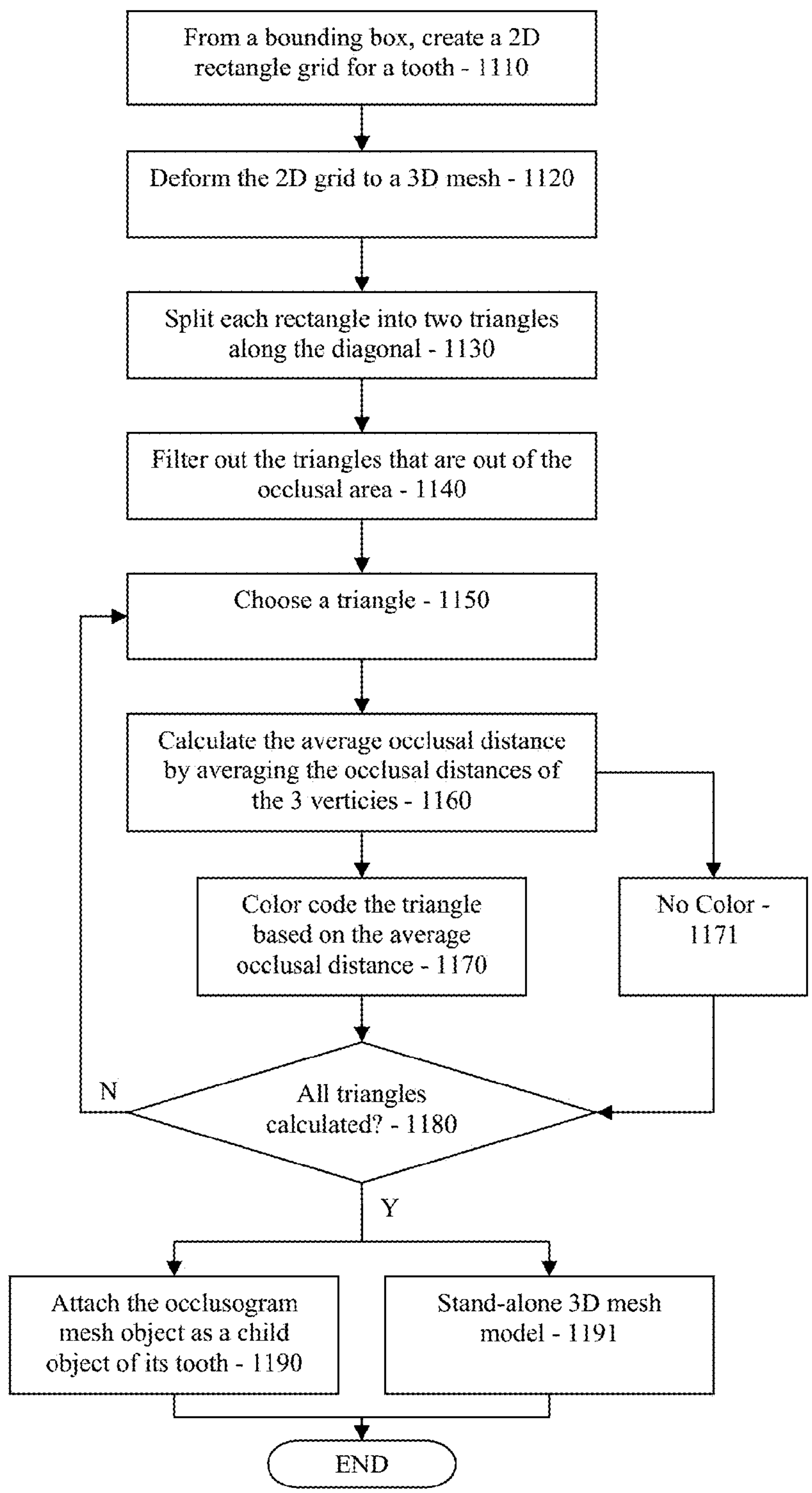
FIG. 11A is a flowchart illustrating 3D occlusogram representation as a 3D mesh object in one aspect based on an embodiment of the present disclosure.
Figure 11B:
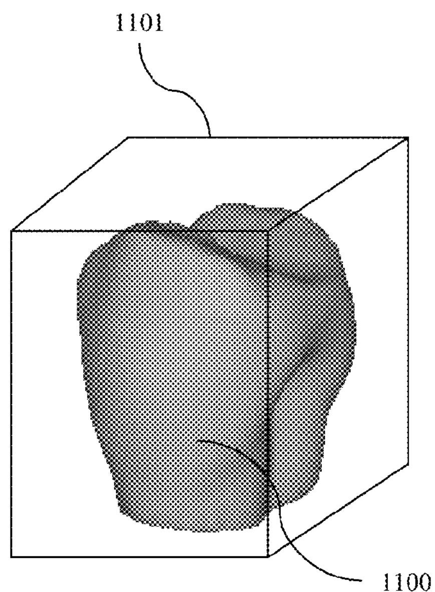
FIG. 11B-11D illustrate steps used in the process shown in FIG. 11A in an embodiment of the present disclosure.
Figure 11C:
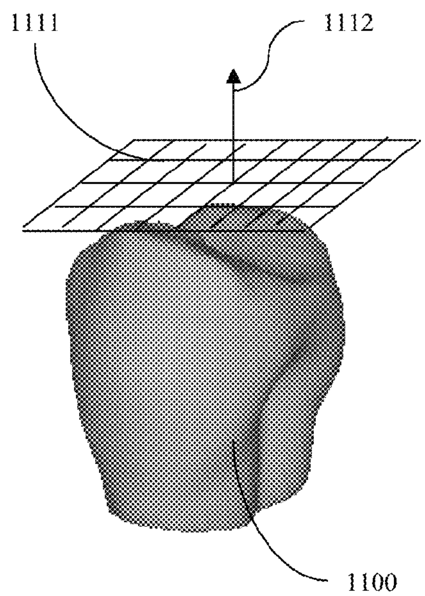
Figure 11D:
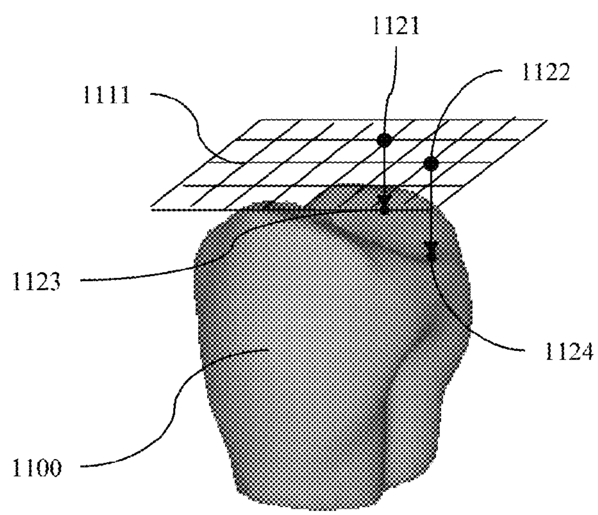

FIG. 11A is a flowchart illustrating 3D occlusogram representation as a 3D mesh object in one aspect based on an embodiment of the present disclosure. FIG. 11B-11D illustrate steps used in the process shown in FIG. 11A in an embodiment of the present disclosure.

Referring to FIGS. 11A-11D, in some embodiments of the present disclosure, occlusal data for a tooth 1100 may be represented as an occlusogram, which may be a virtual 3D mesh model object. To construct a 3D mesh, a 2D grid 1111 may be used as a base. The 2D grid 1111, for example, a rectangle grid, or a grid made up of a plurality of rectangles, can be constructed (FIG. 11A, 1110).

The 2D grid 1111 may be derived from a bounding box 1101 of the tooth 1100 and may be on the occlusal plane, or the plane generally parallel to the biting surface of the tooth. The 2D grid 1111 may have a constant density, or a variable density. The density of the 2D grid 1111 can, for example, be determined by the size of the rectangles in the grid.

In one aspect, it may be desirable to use a variable density 2D grid 1111, with higher density grid sections where the tooth has more contours and critical geometry, and a lower density grid at simpler tooth sections. The higher the density of the grid, the longer it may take to process the model. Thus, in one aspect, it may be desirable to use higher density grid sections where the tooth geometry is more critical and complex. Once the 2D grid 1111 has been established, the nodes 1121,1122 on the 2D grid 1111 may be mapped onto the 3D mesh of the tooth 1123, 1124 in the direction normal 1112 to the 2D grid (FIG. 11A, 1120). The points 1123, 1124 from the 2D grid nodes 1121, 1122 deformed onto the 3D mesh of the tooth 1100 form a rectangular 3D mesh of the tooth.

In some embodiments, each rectangle in the 3D mesh of the tooth can be split along the diagonal of the rectangle into two triangles (FIG. 11A, 1130). Triangles not located in the occlusal area of the tooth can be removed (FIG. 11A, 1140). Of the remaining triangles, a first triangle can be chosen (FIG. 11A, 1150) and the average occlusal distance can be calculated by averaging the occlusal distances of the 3 vertices of the triangle (FIG. 11A, 1160), as described above for example, in conjunction with FIGS. 10A-10B.

Still referring to FIG. 11A, in some embodiments, the triangles of the 3D mesh of the tooth may be color coded, for example, based on the average occlusal distances of the triangles 1170. Colors that may be used for the occlusogram include, but are not limited to, blue, yellow, red, green, orange, and purple and any shade or combination thereof, as well as shades of non-colors such as white, black, and gray. The occlusogram 1171 may not include color, but display the occlusal distance information in other differentiating ways, such as by using numeric values, different types of shading or different patterns or shapes, among other mechanisms.

In various embodiments, once the occlusal distance for the first triangle is calculated and the data is entered into the occlusogram, the process can be repeated for the rest of the triangles of the 3D mesh of the tooth 1180. Once the occlusal data for all the triangles of the 3D mesh has been calculated, the 3D mesh object occlusogram may, for example, be attached directly to the 3D model of the tooth as a child object 1190, or displayed as a stand-alone object 1191. Furthermore, in one aspect, because the occlusogram is attached to the tooth, the occlusogram may dynamically change as a user manipulates tooth position in its virtual representation.

Figure 12:
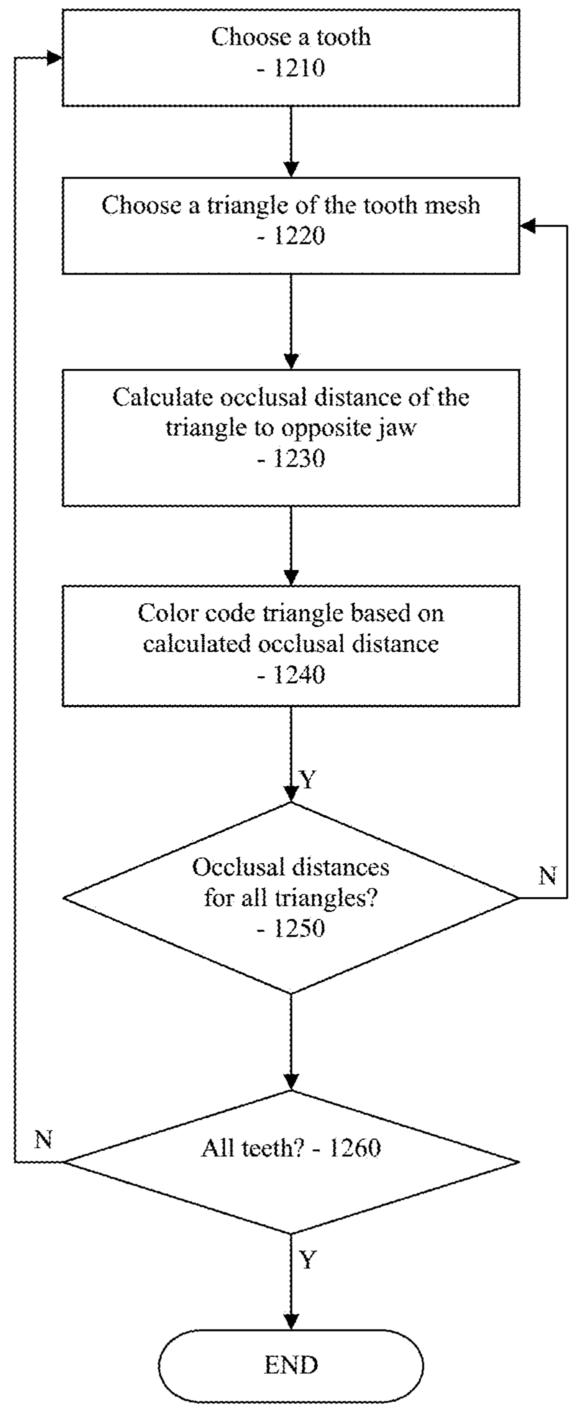
FIG. 12 is a flowchart illustrating a color coded occlusogram representation directly on the surfaces of 3D models of a patient's teeth based on an embodiment of the present disclosure.

FIG. 12 is a flowchart illustrating a color coded occlusogram representation directly on the surfaces of 3D models of a patient's teeth based on an embodiment of the present disclosure. Referring to FIG. 12, in various embodiments of the present disclosure, a first tooth can be chosen from the 3D models of the patient's teeth 1210. From the mesh of the 3D model of the chosen tooth, a first triangle can be chosen 1220. For the chosen triangle, the occlusal distance of the center of the triangle can be calculated, between the chosen tooth and a related tooth on the opposite jaw 1230. The triangles on the tooth surface may then be coded (e.g., color coded) based on the calculated occlusal distance 1240. The calculation and coding of the occlusal distances may be performed for each triangle of the chosen tooth 1250. Once the occlusal distances are calculated, and the coding is completed for the chosen tooth, a next tooth can be chosen and the process can be repeated 1260, for example, until the entire occlusogram for the teeth of the patient has been constructed.

Figure 13A:
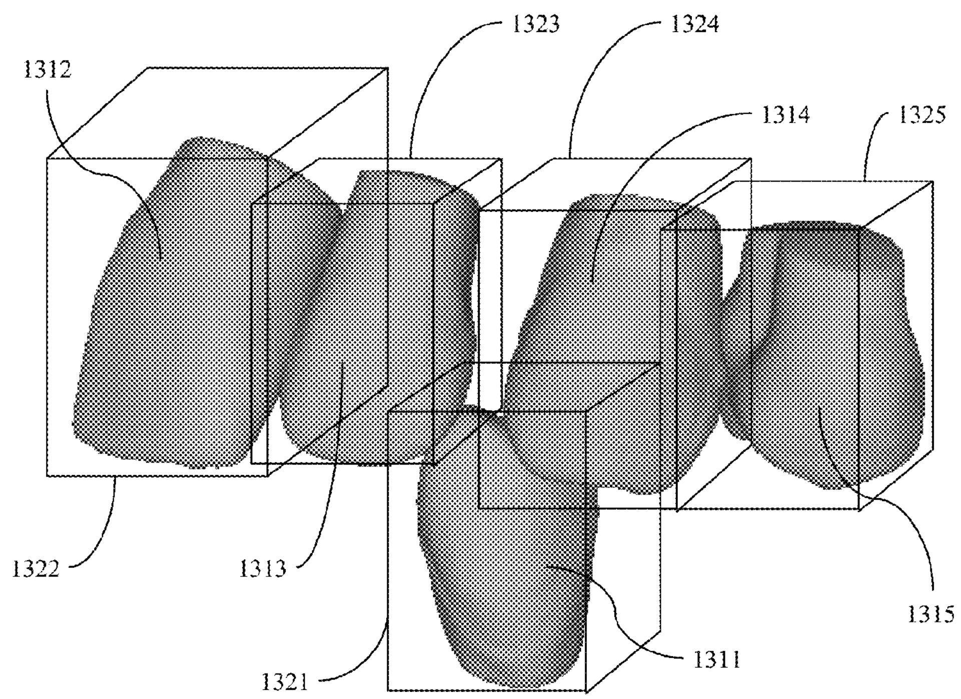
FIGS. 13A-13B illustrate the determining of a potentially occluding teeth list based on an embodiment of the present disclosure.
Figure 13B:
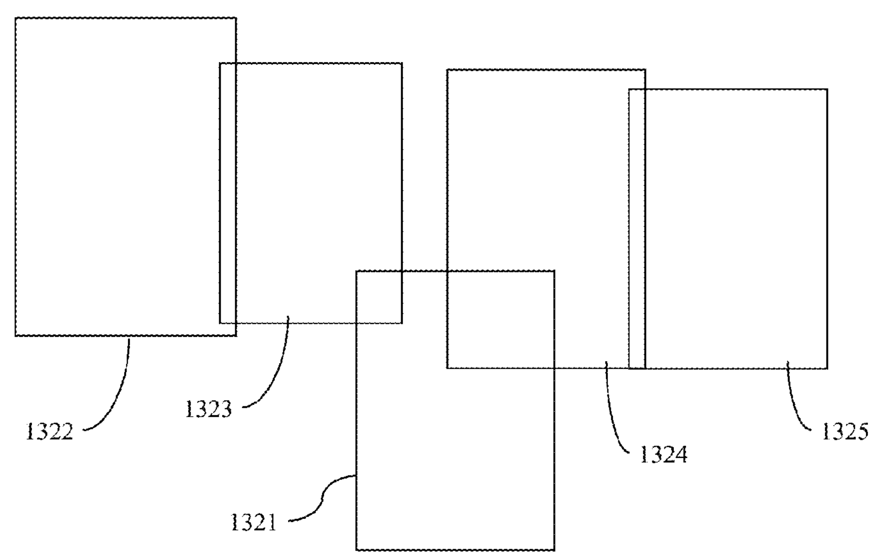

FIGS. 13A-13B illustrate the determining of a potentially occluding teeth list based on an embodiment of the present disclosure. Referring to FIGS. 13A-13B, the occlusion teeth list for a chosen tooth 1311 may be found by looking at the bounding box 1321 for the chosen tooth 1311, as well as the bounding boxes 1322-1325 for other teeth (e.g., 1312-1315) in the vicinity of the chosen tooth 1311.

By determining which teeth 1313-1314 have a bounding box 1323-1324 that overlaps with the bounding box 1321 of the chosen tooth 1311, these teeth can be determined to be the teeth that would make up the occlusion teeth list for the chosen tooth 1311. For example, the determination of overlaps of bounding boxes of teeth may be detected on the 2D occlusal plane as shown in FIG. 13B, among other methods. In FIG. 13B, the bounding boxes are 2D bounding boxes determined by projecting the corresponding 3D bounding boxes in FIG. 13A to a 2D plane.

Figure 14:
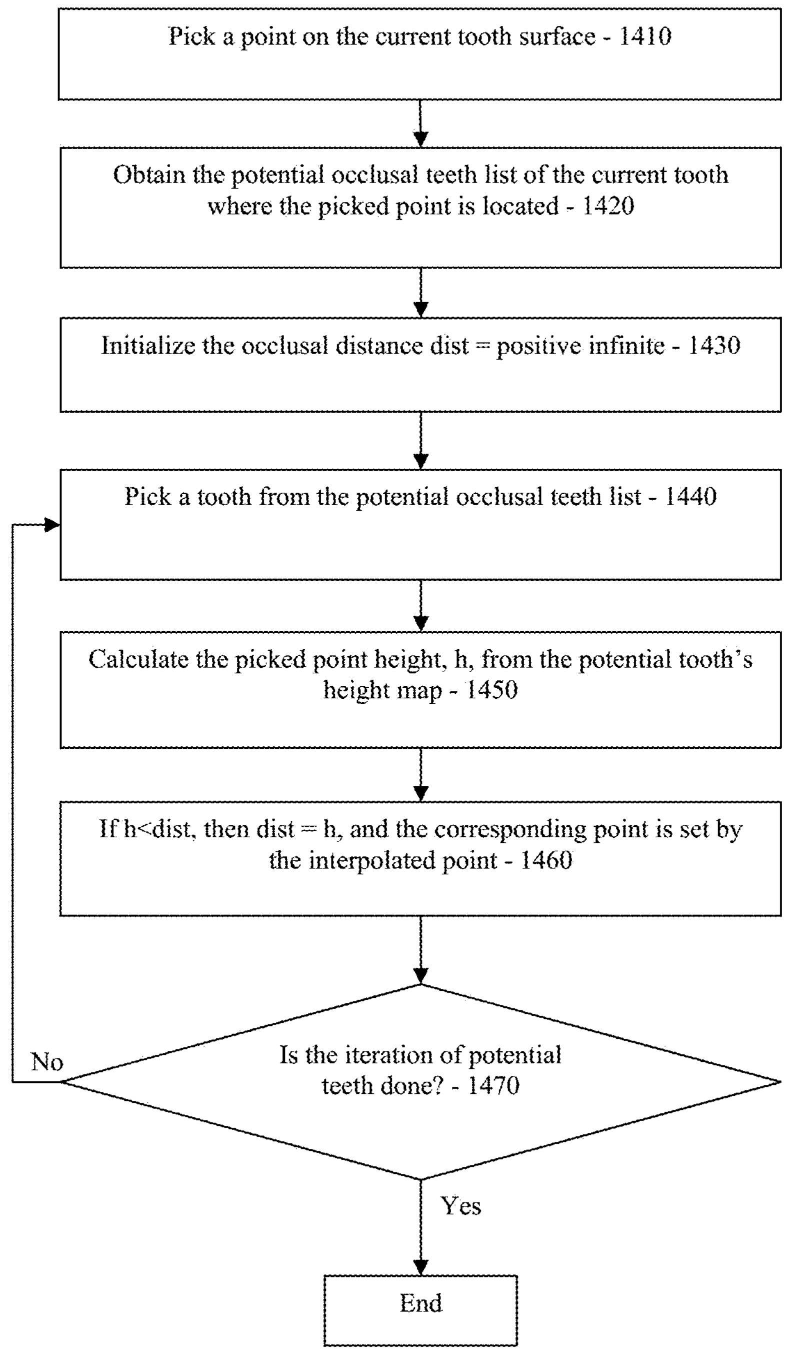
FIG. 14 is a flowchart illustrating auto-locating a related point on the opposite jaw of a point on a tooth based on an embodiment of the present disclosure.

FIG. 14 is a flowchart illustrating auto-locating a related point on the opposite jaw of a point on a tooth based on an embodiment of the present disclosure. Being able to quickly and efficiently locate a related point on a tooth of the opposite jaw from a chosen tooth is desirable in some dental treatments, as it may allow the treatment professional to see which other teeth in the mouth of a patient may be effected by a change in a chosen tooth.

Referring to FIG. 14, in order to auto-locate a corresponding point on the opposite jaw of a patient, a first point can be chosen 1410. The potential occlusal teeth list for the tooth on which the chosen point is located can be obtained in order to narrow the search field to the possible occlusal teeth on the opposite jaw 1420. This may accelerate the process of auto-locating the related point, as it can allow the routine or algorithm to avoid searching teeth that the related point is not located on.

Referring back to FIG. 14, the occlusal distance can be initialized to positive infinite 1430 and a first tooth can be chosen from the potential occlusal teeth list 1440. The height of the chosen point can be calculated from the height map of the tooth on which the chosen point is located, and the distance, h, to the height map of the potential occlusal tooth can be determined 1450. If the distance, h, is smaller than the current occlusal distance, then the occlusal distance equals h, and the corresponding point can be set by the interpolated point 1460. This process can then be repeated for all potential occlusal teeth on the potential occlusal teeth list 1470 until the correct corresponding point is found.

Figure 15:
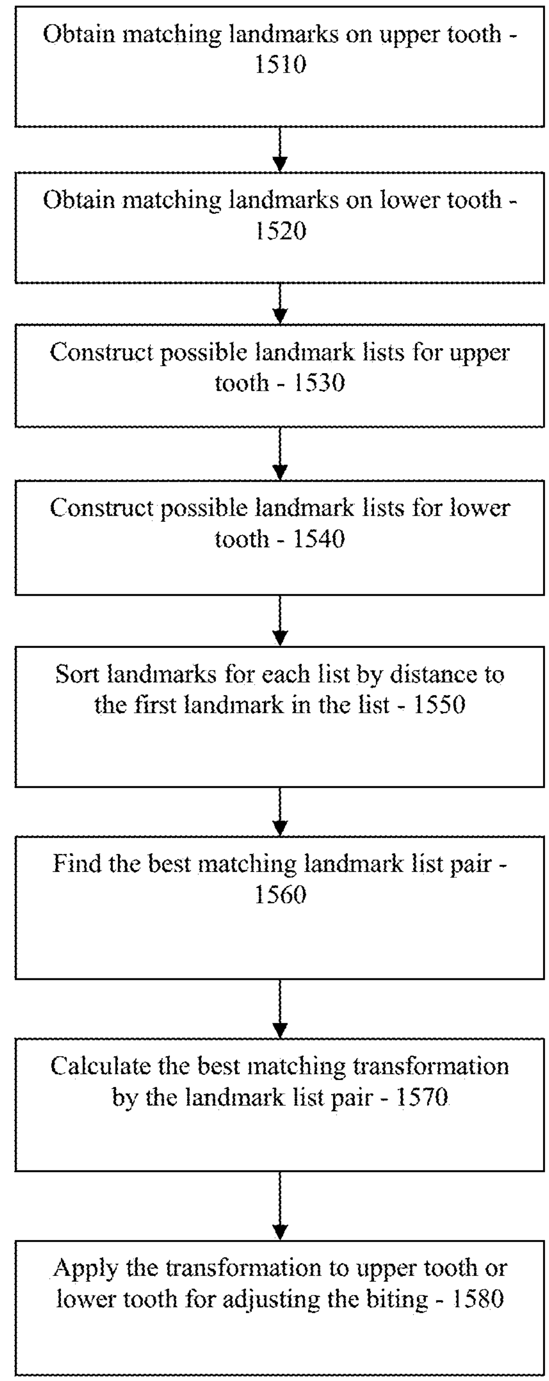
FIG. 15 is a flowchart illustrating calculating a bite adjustment by specifying matching points on the current and opposite jaws based on an embodiment of the present disclosure.

FIG. 15 is a flowchart illustrating calculating a bite adjustment by specifying matching points on the current and opposite jaws based on an embodiment of the present disclosure. Referring to FIG. 15, in some embodiments of the present disclosure, the adjustment of the bite of a patient may be determined by specifying matching points of the current jaw and opposite jaw.

In order to adjust the bite of a patient, the treatment professional may specify the landmarks on both the upper tooth 1510 and the lower tooth 1520. The landmarks can be used to specify the contact points between upper tooth and lower tooth.

When the treatment professional locates the landmarks on the teeth, the contact relationship or contact point pair does not necessarily need to be explicitly specified. In this manner, an algorithm or routine may be designed to determine contact point pair for the best matching landmarks.

Referring back to FIG. 15, in various embodiments, once landmarks are located, landmark lists for the upper tooth 1530 and lower tooth 1540 can be constructed. If n, where n>2, landmark points are specified on the tooth, there can be n possible landmark lists.

Each list can, for example, be identified by the first landmark point. For example, if 4 landmark points, A, B, C, and D are specified on a tooth, the possible landmark lists can be (A, B, C, D), (B, A, C, D), (C, A, B, D), or (D, A, B, C). For each landmark list, the landmarks can be sorted by distance to the first landmark on the list 1550.

For sorting each possible landmark point list, the order of points in the list can be determined by its distance to the first point, i.e. the reference point. The point list can, for example, be sorted in an ascending order. For example, in the landmark point list (A, B, C, D), if D is the first closest point to point A, B is the second closest point to point A, and C is the third closest point to point A, the landmark point list, (A, B, C, D) can be sorted as (A, D, B, C).

Based on the sorted possible upper tooth's landmark lists and the sorted possible lower tooth's landmark lists, a best matching landmark list pair can be found 1560. In one aspect, the criterion for the best matching landmark pair can, for example, include minimizing the sum of squared distance error, using a least-square error metric.

The distance error can be the distance difference of a point pair. As used herein, in a point pair, one point is from the upper landmark list, and the other is from the lower landmark list. Two points in the point pair have the same order index.

After having the best matching landmark list pair, the best matching rigid transformation between the two landmark lists may be determined 1570. The transformation can be calculated by certain algorithms, such as singular value decomposition (SVD), quaternions, orthonormal matrices, and/or dual quaternions. Once the transformation is calculated, it may be applied to the upper and/or lower tooth for adjusting the bite of the patient 1580.

Figure 16:
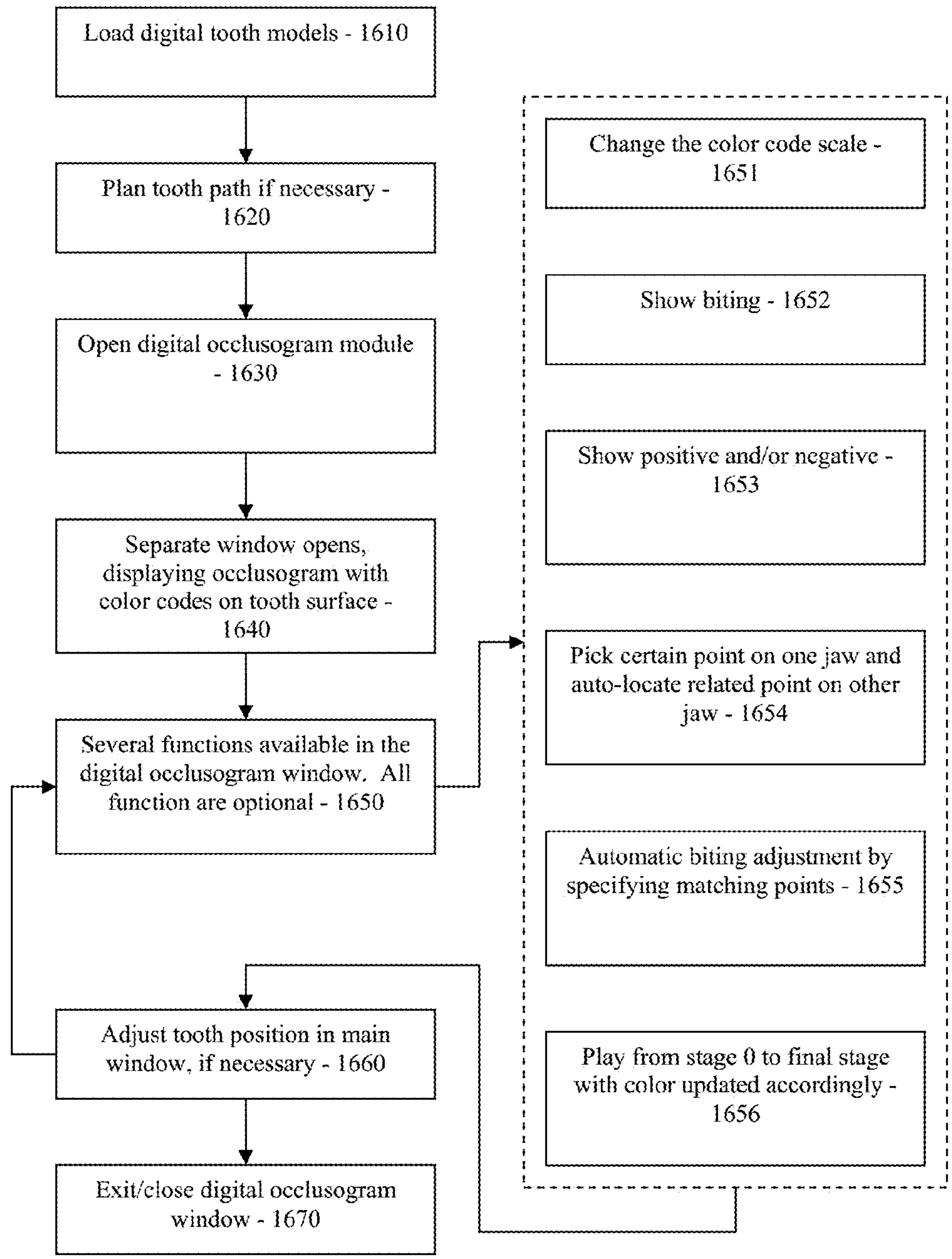
FIG. 16 is a flow chart illustrating the use of an occlusogram in virtual treatment planning in one aspect based on an embodiment of the present disclosure.

FIG. 16 is a flow chart illustrating the use of an occlusogram in virtual treatment planning in one aspect based on an embodiment of the present disclosure. Referring to FIG. 16, a virtual occlusogram may be used in conjunction with programs for simulating the dental treatment of teeth.

Virtual treatment planning may begin with loading virtual tooth models into a simulation program 1610. Virtual tooth models may be acquired through various means, including, but not limited to, digitization of a patient's teeth via processes such as X-ray, magnetic resonance imaging (MRI), or interoral scanning of a patient's teeth directly or of a mold of a patient's teeth.

In some cases, a treatment plan may have already been decided upon for the patient by a treatment professional. If a treatment plan has already been determined, a simulation of the treatment plan may be applied, which can, for example, determine a planned tooth path 1620. Regardless of whether a preferred treatment plan has been decided upon, once the virtual models of a patient's teeth are loaded into the program, the virtual occlusogram module may be opened 1630.

Referring to FIG. 16, in some embodiments, the virtual occlusogram module may open in a separate computing device program window 1640. The virtual occlusogram may be a 3D mesh object overlaid on top of the 3D model of the patient's teeth, and coded to represent the occlusal distances at various points on the tooth.

In various embodiments, the occlusogram window may be a viewing window, separate from the main treatment window in which tooth position and/or treatment options may be changed. The occlusogram window may have several available functions 1650, including, but not limited to, a function to change the code scale 1651, an option to show the biting, upper jaw, or lower jaw 1652, an option to display either a partial mesh with positive occlusal distance, a partial mesh with negative occlusal distance, or a complete mesh 1653, an option to pick a certain point on one jaw and auto-locate the relating point on the other jaw 1654, an option for automatic bite adjustment based on specified matching points 1655, and/or an option to show each stage of the treatment from the beginning to the final stage with the codes relating to the occlusal distance updating accordingly 1656.

Furthermore, the occlusogram may be updated based on adjusted tooth positions in the main treatment window 1660. In some embodiments of the present disclosure, the occlusal information, and, from that, the virtual 3D occlusogram model, including the codes for occlusal data information, may be updated in real-time as the position of teeth on either jaw of the patient is updated. In various embodiments, once the treatment simulation is finished, and a final treatment procedure and treatment goals are decided upon, the occlusogram module may then be exited and the occlusogram window closed.

Figure 17:
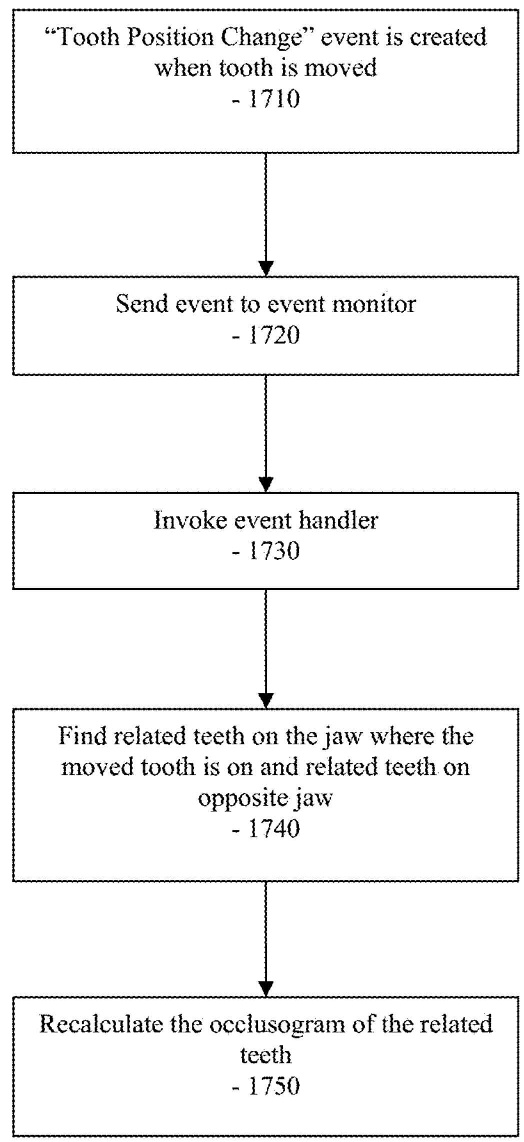
FIG. 17 is a flowchart illustrating dynamically generating an occlusogram in one aspect based on an embodiment of the present disclosure.

FIG. 17 is a flowchart illustrating dynamically generating an occlusogram in one aspect based on an embodiment of the present disclosure. During the virtual treatment planning, a treatment professional may need to specify a tooth's gradual movements from a original tooth's position to a tooth's final setup position.

The treatment plan may be separated into a number of treatment stages. In the process of teeth moving from their original positions to their final positions, the occlusal information may change. A treatment professional may need to check the occlusal relationship at each stage to make sure the occlusal relationship is, for example, reasonable or within a certain predetermined threshold. If it is not reasonable, adjustment may be needed to modify the position of one or more teeth.

In some embodiments of the present disclosure, the occlusogram can be dynamically updated at each stage of treatment and/or when a tooth position is changed. When a treatment stage is changed, tooth position for a number of teeth may change also. Furthermore, in one aspect, the tooth position may be interactively adjusted at any stage. In various embodiments, the occlusogram may be generated and updated dynamically in real-time at each stage of treatment.

Referring to FIG. 17, in some embodiments, each time a tooth is determined to have moved in the virtual model, a "Tooth Position Change" event may be created or generated 1710. This movement may, for example, be the result of a treatment profile moving on to a next stage and thus resulting in the movement of one or more teeth, or may be the result of a user manually re-positioning a tooth or changing the treatment profile in order to achieve different results.

In some embodiments, once the "Tooth Position Change" event is created, a notice of the event can be sent to an event monitor 1720. The event monitor may keep track of changes in tooth position due to treatment profile stage changes or changes made by the user of the virtual model.

In various embodiments, each event recorded in the event monitor can invoke an event handler 1730. The event handler may find any related teeth on the same jaw as the moved tooth and/or the opposite jaw 1740. Once a list of related teeth has been established by the event handler, the virtual occlusogram may be recalculated for the teeth on the related teeth list 1750 and the occlusogram display may be updated in real-time for the user to view the effect of the tooth movement.

Accordingly, in accordance with various aspects of the present disclosure, a dynamic, real-time updated 3D occlusogram is provided for modeling tooth movement, for example, in the course of dental treatment to correct one or more malocclusions or non-optimal positioning of a patient's teeth. More specifically, some embodiments of the present disclosure methods of determining occlusal information for the teeth of a patient are disclosed. This can, for example, include the height maps and/or distance field of the crown of a patient's teeth, occlusal distances based on the space and collision depth between the teeth on a jaw and the teeth on its opposing jaw, and/or determining lists of potential occluding teeth.

Some embodiments of the present disclosure disclose a 3D occlusogram including a virtual 3D model of the teeth and bite of a patient. More specifically, the 3D occlusogram may show the relationship between teeth and the upper and lower jaws of a patient, and can include when the jaws are in a closed position. The 3D occlusogram may be an add-on module for simulation and dental treatment CAD (Computing device Aided Design) programs or it may be a stand alone program for use in any dental treatment procedure.

The 3D occlusogram may, for example, be used for diagnostic purposes, such as determining malocclusions of a patient's teeth and/or bite, including open bite, overbite, under bite, and overjet, and also for determining bite angles, for example, the mandibular plane, or lower jaw, angle. Furthermore, the 3D occlusogram may be used as a reference for treatment planning.

Accordingly, a computing device program product embodiment can include a medium readable by a computing device, the computing device readable medium having computing device executable instructions adapted to: determine a virtual three dimensional (3D) mesh model object of at least one tooth of a patient, display the determined virtual 3D mesh model object of at least one tooth of a patient, where the 3D mesh model object includes a plurality of data sets associated with a set of occlusal information for the at least one tooth of the patient.

The computing device executable instructions may be adapted to overlay the virtual 3D mesh model object over a virtual 3D model of at least one tooth of the patient. The computing device executable instructions may be adapted to model one or more dental treatments on the at least one tooth of the patient.

The computing device executable instructions may be adapted to display the plurality of data sets associated with the set of occlusal information as one or more coded portions on the 3D mesh model object. Also, the computing device executable instructions may be adapted to modify a resolution of the virtual 3D mesh model.

Additionally, the computing device executable instructions may be further adapted to generate a multiple resolution 3D mesh model associated with a variation of tooth surface curvature. Moreover, the computing device executable instructions may be adapted to dynamically update the virtual 3D mesh model object in response to one or more input parameters associated with the one or more dental treatments on at least one tooth.

In a further aspect, the computing device executable instructions may be adapted to display the 3D mesh model object in a separate program window from a main treatment window, where the computing device executable instructions may be further adapted to display the data sets relating to the set of occlusal information as one or more predetermined codes on the 3D mesh model object. Additionally, the computing device executable instructions may be adapted to update the virtual 3D mesh model object in response to one or more detected changes during the simulation of the one or more dental treatments on at least one tooth of the patient.

A method in accordance with an embodiment of the present disclosure, can for example, include obtaining virtual tooth models of an upper jaw and a lower jaw of a patient, viewing one or more occlusal information data sets associated with the virtual tooth models via a display of a computing device, selecting a dental treatment process, simulating the selected dental treatment process on the virtual tooth models, and applying the simulated dental treatment process to one or more teeth of the patient.

In some embodiments, the occlusal information data sets may include the space or collision depth between the upper teeth and lower teeth. Also, the occlusal information data sets may be displayed as a virtual 3D mesh object, where the virtual 3D mesh object may be overlaid on top of the virtual tooth model.

A method may include defining a resolution of the virtual tooth models, where the defined resolution may include a plurality of resolutions. Further, the defined plurality of resolutions may be associated with a tooth surface curvature variation.

The occlusal information data sets may be displayed as a color code set on the virtual 3D mesh object, where the color code set may be variable, and further, the color code set may be updated (automatically, based on pre-programming, and/or manually) in response to a detected change in the position of the tooth in the virtual tooth models.

The virtual 3D mesh may be displayed as one or more of a partial mesh with a positive occlusal distance, a partial mesh with a negative occlusal distance, or a complete mesh. Moreover, a related point on the opposite jaw may be automatically identified in response to a selection of a point on a tooth. Methods may include specifying matching points on a tooth on the upper jaw and the lower jaw of the patient to adjust the bite of a patient.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A non-transitory computing device readable medium having executable instructions which can be executed by a processor to cause a computing device to perform a method, comprising:

determining a plurality of data sets associated with a set of occlusal information for at least one tooth of a patient, wherein determining a data set includes calculating an average occlusal distance of at least one triangle of a three dimensional (3D) mesh of the at least one tooth using at least one of a height map and a distance field of the at least one tooth;

determining a virtual 3D mesh model object of the at least one tooth using the plurality of data sets; and displaying the determined virtual 3D mesh model object of the at least one tooth of a patient.

2. The medium of claim 1, wherein the height map includes a two-dimensional (2D) array data structure that stores a vertical height of a crown surface of the at least one tooth.

3. The medium of claim 1, wherein the distance field includes a 3D array data structure corresponding to a 3D grid with generators defined by a bounding box of the at least one tooth.

4. The medium of claim 1, wherein the executable instructions are executed by the processor to cause the computing device to perform the method comprising building the height map of the at least one tooth.

5. The medium of claim 4, wherein building the height map of the at least one tooth comprises determining a bounding box of a 3D mesh of the at least one tooth.

6. The medium of claim 4, wherein building the height map of the at least one tooth comprises:

scanning triangles from a list of polygon surfaces comprising the 3D mesh of the at least one tooth to determine height values for the at least one tooth; and inputting the determined height values in the height map.

7. The medium of claim 6, wherein scanning a first triangle from the list comprises:

determining a bounding box of the first triangle on a two-dimensional planar grid;

selecting a first grid node of the triangle;

projecting the first grid node into the triangle as a projected point; and calculating a height of the first grid node using the projected point.

8. The medium of claim 1, wherein the executable instructions are executed by the processor to cause the computing device to perform the method comprising:

calculating a height of a point in a cell of a height map coordinate system of the height map based at least on a distance between the point and a line formed by two corner points of the cell.

9. The medium of claim 1, wherein the executable instructions are executed by the processor to cause the computing device to perform the method comprising building the distance field comprising:

initializing a closest distance component to a value of a height of a corresponding node of the 3D grid for all elements of the 3D array; and scanning each triangle of the 3D mesh of the at least one tooth.

10. The medium of claim 9, wherein the executable instructions are executed by the processor to cause the computing device to perform the method comprising:

calculating a closest distance for points between nodes on the 3D grid using multi-linear interpolation of the corresponding values of the nodes of the 3D grid to build the distance field.

11. A non-transitory computing device readable medium having executable instructions which can be executed by a processor to cause a computing device to perform a method, comprising:

determining a plurality of data sets associated with a set of occlusal information for at least one tooth of a patient, wherein determining a data set includes calculating an average occlusal distance of at least one triangle of a three dimensional (3D) mesh of the at least one tooth using at least one of a height map and a distance field of the at least one tooth;

determining a virtual 3D mesh model object of the at least one tooth using the plurality of data sets; and simulating a dental treatment process using the virtual 3D mesh model object of the at least one tooth.

12. The medium of claim 11, wherein the executable instructions are executed by the processor to cause the computing device to perform the method comprising updating the virtual 3D mesh model object in response to one or more detected changes during the simulation of the dental treatment process.

13. The medium of claim 11, wherein the executable instructions are executed by the processor to cause the computing device to perform the method comprising automatically identifying a related point on an opposite jaw in response to a selection of a point on the at least one tooth.

14. The medium of claim 11, wherein the executable instructions are executed by the processor to cause the computing device to perform the method comprising specifying matching points on a tooth on a upper jaw and a lower jaw of the patient to adjust the bite of the patient.

15. The medium of claim 11, wherein the executable instructions are executed by the processor to cause the computing device to perform the method comprising dynamically changing in real time the virtual 3D mesh object as a portion of a virtual tooth model of the at least one tooth is manipulated during the simulated dental treatment process.

16. A computing system, comprising:

a memory having executable instructions stored thereon; and a processor coupled to the memory and configured to execute the instructions to:

determine a plurality of data sets associated with a set of occlusal information for at least one tooth of a patient, wherein determining a data set among the plurality of data sets includes instructions executed to:

map nodes from a surface grid of the at least one tooth to a three dimensional (3D) mesh of the at least one tooth to form a rectangular 3D mesh of the tooth;

split at least one rectangle in the rectangular 3D mesh along a diagonal into two triangles; and calculate an average occlusal distance of the at least one triangle using at least one of a height map and a distance field of the at least one tooth;

determine a virtual 3D mesh model object of the at least one tooth using the plurality of data sets; and display the determined virtual 3D mesh model object of the at least one tooth of the patient.

17. The system of claim 16, wherein the instructions to calculate the average occlusal distance of the at least one triangle include instructions executed by the processor to determine the triangle is in an occlusal area of the at least one tooth.

18. The system of claim 16, wherein the processor is configured to execute the instructions to display the plurality of data sets as a color code set on the virtual 3D mesh model object.

19. The system of claim 18, wherein the processor is configured to execute the instructions to update the color code set in response to a detected change during a simulation of a dental treatment on the at least one tooth.

20. The system of claim 16, wherein the processor is configured to execute the instructions to display the determined virtual 3D mesh object as one or more of a partial mesh with a positive occlusal distance, a partial mesh with a negative occlusal distance, or a complete mesh.

* * * * *